(12) United States Patent
Hillairet et al.

(10) Patent No.: US 7,842,829 B2
(45) Date of Patent: Nov. 30, 2010

(54) CATALYST SYSTEMS BASED ON AROMATIC DIIMINE LIGANDS

(75) Inventors: Caroline Hillairet, Soignies (BE); Guillaume Michaud, Lille (FR); Sirol Sabine, Horrues (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 0 days.

(21) Appl. No.: 11/994,960

(22) PCT Filed: Jul. 6, 2006

(86) PCT No.: PCT/EP2006/063990

§ 371 (c)(1),
(2), (4) Date: Aug. 1, 2008

(87) PCT Pub. No.: WO2007/006737

PCT Pub. Date: Jan. 18, 2007

(65) Prior Publication Data

US 2009/0131615 A1   May 21, 2009

(30) Foreign Application Priority Data

Jul. 7, 2005   (EP) .................................. 05106165

(51) Int. Cl.
C07F 15/00 (2006.01)
C07F 15/02 (2006.01)
C07F 15/04 (2006.01)
C07F 11/00 (2006.01)

(52) U.S. Cl. ............................ 556/138; 556/57; 556/51; 556/42; 556/45

(58) Field of Classification Search ................. 556/138, 556/57, 51, 42, 45
See application file for complete search history.

(56) References Cited

PUBLICATIONS

Vedder et al., Eur. J. Inorg. Chem., 2005, 1071-1080.*
Reetz et al., J. Am. Chem. Soc., 2000, 122, 996-997.*
Benaglia et al., Tetrahedron Letters, 2004, 45, 8705-8708.*
Suga et al., Bull. Chem. Soc. Jpn., 2003, 76, 189-199.*
Reetz, "Chiral Diketimines as Ligands in Pd-Catalyzed Reactions: Prediction of Catalyst Activity by the AMS Model" Journal of the American Chemical Society 122(5), 996-997, 2000.
Kettunen, "Alternative Coordination Modes in Palladium(II)-Diimino-bispyridine Complexes with an Axially Chiral biphenyl Backbone" European Journal of Inorganic Chemistry, 2005, 1081-1089.
Vedder, Chiral Iron and Cobalt Complexes with Biphenyl-Bridged Bis(pyridylimine) Ligands-Syntheses, Structures and Reactivities: European Journal of Inorganic Chemistry, 2005, 1071-1080.
Benaglia, "Enantioselective addition of phenyl and alkyl acetylenes to imines catalyzed by chiral Cu(I) complexes" Tetrahedron Letters, Elsevier, Amsterdam, 2004, 45(47), 8705-8708.
Suga, "Assymmetric Cyclopropanation and Aziridination Reactions of Olefins Catalyzed by Cu(I)-Binaphtyldiimine Complexes" Bull. Chem. Soc. Jpn., 2003, 76(1) 189-199.

* cited by examiner

*Primary Examiner*—Rip A. Lee
(74) *Attorney, Agent, or Firm*—Tenley R. Krueger (57) ABSTRACT

The present invention discloses the use of aromatic diamine ligands to prepare catalyst systems suitable for the oligomerization or polymerization of ethylene and alpha-olefins.

5 Claims, 1 Drawing Sheet

FIG. 1

CATALYST SYSTEMS BASED ON AROMATIC DIIMINE LIGANDS

CROSS-REFERENCE TO RELATED APPLICATIONS

This application claims the benefit of PCT/EP2006/063990, filed Jul. 6, 2006, which claims priority from EP 05106165.3, filed Jul. 7, 2005.

The present invention relates to the field of single site catalyst systems based on diimine ligands and suitable for oligomerising or polymerising ethylene and alpha-olefins.

There exists a multitude of catalyst systems available for polymerising or oligomerising ethylene and alpha-olefins, but there is a growing need for finding new systems capable to tailor polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., Chem. Rev. 2003, 103, p. 283). But there is still a need to improve either the specificities or the performances of these systems.

It is an aim of the present invention to provide a new catalyst components based on aromatic diimine ligands.

It is another aim of the present invention to provide active catalyst systems based on these catalyst components.

It is a further aim of the present invention to provide a process for polymerising or for oligomerising ethylene and alpha-olefins with these new catalyst systems.

It is also an aim of the present invention to provide a bi- or multi-modal polyethylene by polymerising ethylene with these new catalysts systems.

Accordingly, the present invention discloses a ligand of general formula I

(I)

resulting from the condensation reaction between diamine of formula (II)

(II)

and a ketone or aldehyde of formula (III)

(III)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, unsubstituted or substituted hydrocarbyl, or inert functional group. Two or more of those groups can themselves be linked together to form further ring or rings.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula —OR* wherein R* is unsubstituted or substituted hydrocarbyl. After metallation of the ligand, an inert functional group must not coordinate to the metal more strongly than the groups organised to coordinate to the metal and thereby displace the desired coordinating group.

Preferably, $R_5$, $R_6$, $R_7$, $R_8$, $R_9$, $R_{10}$, $R_{11}$ and $R_{12}$ are each independently selected from hydrogen, unsubstituted or substituted alkyl groups, unsubstituted or substituted aryl groups, or unsubstituted or substituted cycloalkyl groups and if they are substituted, the substituents may be joined to form a closed structure. Most preferably, $R_5$, $R_6$, $R_{11}$ and $R_{12}$ are the same and they are hydrogen, and $R_7$ and $R_8$ together, as well as $R_9$ and $R_{10}$ together, are joined to form unsubstituted naphtyl groups.

Preferably $R_1$, $R_2$, $R_3$ and $R_4$ are hydrogen, unsubstituted or substituted alkyl groups, unsubstituted or substituted aryl groups, or unsubstituted or substituted cycloalkyl groups, more preferably, they are unsubstituted or substituted phenyl groups and if they are substituted, the substituents may be joined to form a closed structure. If the phenyls are substituted, the substituents preferably occupy 2 and 6 positions. Some of the preferred substituents on the phenyl groups, according to the present invention, are one Cl in position 4 or two Cl respectively in positions 4 and 6, or two methyl groups respectively in positions 2 and 6, or three methyl groups respectively in positions 2, 4 and 6 or one methoxy group in position 4, or two methoxy groups respectively in positions 4 and 6, or two trifluoromethyl groups respectively in positions 2 and 5, or two nitro groups respectively in positions 2 and 6, or fluorenyl substituents. The most preferred substituted phenyl groups have two methyl groups respectively in positions 2 and 6, or three methyl groups respectively in positions 2, 4 and 6 or one methoxy group in position 4 or two methoxy groups respectively I, positions 4 and 6.

The invention also discloses a catalyst component of formula IV that is the condensation reaction product of the ligand of formula I wherein $R_1$, $R_2$, $R_3$, $R_4$, $R_5$, $R_6$, $R_7$, $R_8$, $R_9$, $R_{10}$, $R_{11}$ and $R_{12}$ are as described here-above, and a metallic salt of formula $MX_n$ in a solvent, wherein M is a metal Group 3 to 10 of the periodic Table, X is the same or different and can be an organic or inorganic monovalent ligand, preferably a halogen, alcoholate, carboxylate or substituted or unsubstituted hydrocarbyl and n is the valence of M and is 1, 2, 3 or 4.

Preferably, M is Ti, Zr, Hf, V, Cr, Mn, Fe, Co, Ni, Pd or rare earths. More preferably, it is Cr or Ni.

The solvent may be selected from dichloromethane or tetrahydrofuran and the condensation reaction is carried out at room temperature or at reflux.

The present invention also discloses an active catalyst system comprising the single site catalyst component of formula IV and an activating agent having an ionising action.

Suitable activating agents are well known in the art. The activating agent can be an aluminium alkyl represented by formula $AlR^+{}_nX_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula for oligomeric, linear aluminoxanes and by formula for oligomeric, cyclic aluminoxane,
wherein n is 1-40, preferably 1-20, m is 3-40, preferably 3-20 and R* is a $C_1$-$C_8$ alkyl group and preferably methyl or isobutyl.

Preferably, the activating agent is methylaluminoxane (MAO) or tetra-isobutyldialuminoxane (IBAO), more preferably, it is IBAO.

The amount of activating agent is selected to give an Al/M ratio of from 100 to 3000, preferably of from 500 to 2000. The amount of activating agent depends upon its nature: for IBAO the preferred Al/M ratio is of about 500, and for MAO, it is about 2000.

Suitable boron-containing activating agents may comprise a triphenylcarbenium boronate such as tetrakis-pentafluorophenyl-borato-triphenylcarbenium as described in EP-A-0427696, or those of the general formula [L'-H]+ [$BAr_1Ar_2X_3X_4$]— as described in EP-A-0277004 (page 6, line 30 to page 7, line 7). The amount of boron-containing activating agent is selected to give B/M ratio of from 0.5 to 5, preferably of about 1.

In an other embodiment, according to the present invention, the single site catalyst component of formula IV may be deposited on a conventional support. Preferably, the conventional support is silica impregnated with MAO. Alternatively and preferably, it can be an activating support such as fluorinated alumina silica.

The present invention further discloses a method for preparing an active catalyst system that comprises the steps of:
  a) providing a diamine ligand precursor of formula II;
  b) carrying out a condensation reaction of diamine ligand precursor II of step a) with a ketone or aldehyde of formula III;
  c) complexing the ligand obtained in step b) with a metallic salt;
  d) retrieving a catalyst component of formula IV;
  e) activating with an activating agent having an ionising action;
  f) optionally adding a cocatalyst
  g) retrieving an active oligomerisation or polymerisation catalyst system.

Alternatively, in step e) catalyst component IV is deposited on a support impregnated with an activating agent or on an activating support containing fluor.

The cocatalyst may be selected from triethylaluminium, triisobutylaluminum, tris-n-octylaluminium, tetraisobutyldialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
a) injecting the active catalyst system into the reactor;
b) injecting the monomer and optional comonomer either before or after or simultaneously with step a);
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

In another preferred embodiment according to the present invention, the optional comonomer is a polar functionalised alpha-olefin.

The present invention also discloses a bi- or multi-modal polyethylene obtained by polymerising ethylene with an active catalyst system described hereabove. In a first preferred embodiment the active catalyst system comprises a component of formula IV wherein M is Cr and IBAO as activating agent: it produces bimodal polyethylene. In a second preferred embodiment, the active catalyst system comprises a component of formula IV wherein M is Cr and MAO as activating agent: it produces multimodal polyethylene The bi- or multi-modal polyethylene is characterized by a Mw value between 450 KDa and 900 Kda, and a melting temperature between 132° C. and 135° C. The polymer has no short chain branching detectable by $^{13}C$ NMR analysis. It has methyl and isobutyl ends. It also has long chain branching. The presence of the long chain branching is indicated by rheological technique.

Throughout this description, LCB means chains long enough for entanglements to occur.

In order to quantify LCB concentration with rheology, we have adapted Shroff and Mavridis definition of LCBI (Long Chain Branching Index) to our high molecular weight PE samples. (R. N. Shroff and H. Mavridis, Macromolecules, 32, 8454, 1999.) As explained by those authors, LCBI quantifies the Theological effect of LCB (enhancement of shear viscosity at low shear rates) for narrow and broad molecular weight distribution (MWD) samples with sparse amount of LCB, that is LCB concentration typically too low to be detected by 13C NMR (for homopolymers PE) or by solution techniques such as size exclusion chromatography (SEC) coupled with on-line viscosity or light scattering detectors. DRI (Dow Rheology Index) which is another LCB indicator described in lai et al. (S. Lai, T. A. Plumley, T. I. Butler, G. W. Knight, C. I. Kao, SPE Antec Techn. Papers, 40, 1814, 1994) is not suitable to quantify LCB in polyethylene resins with polydispersity index larger than 4. DRI is thus not suitable to gauge LCB in our PE resins with broad MWD.

According to those authors, LCBI is defined as the ratio of intrinsic viscosities of PE resins estimated by rheology to that determined via solution techniques.

$$LCBI = \frac{[\eta]_{rheo}}{[\eta]_{sol}} - 1$$

wherein $[\eta]_{rheo}$ and $[\eta]_{sol}$ are the intrinsic viscosities obtained respectively from rheology or via solution.

Thus, LCBI is zero for linear samples and is above zero for polyethylene containing long chain branching. A high level of LCB is encountered with LCBI above 0.8. Instead of determining intrinsic viscosity from the relative viscosity at 0.2 dg/min as explained in their publication, we calculate intrinsic viscosity value via solution (expressed in dl/g) in terms of weight average molecular weight Mw (expressed in Da) obtained by size exclusion chromatography (SEC) with equation $$[\eta]_{sol} = 5.25 * 10^{-4} (M_w)^{0.76}$$

Zero shear viscosity ($\eta_0$) (expressed in Pa·s) is also related to $M_w$ (expressed in Da) by equation $$\eta_0 = 3.834 * 10^{-16} (M_w)^{3.855}$$

Zero shear viscosity is estimated by fitting with Carreau-Yasuda flow curve at 190° C., obtained by oscillatory shear rheology on ARES equipment in the linear viscoelasticity domain. Circular frequency (W in rad/s) varies from 0.05-0.1 rad/s to 250-500 rad/s and the shear strain is typically 10%.

The intrinsic viscosity inferred from rheology can thus be expressed as $$\eta = \eta_0/(1+(W^*\tau)^b)^{((1-n)/b)}$$

wherein $\tau$, b and n are fitting parameters called relaxation time, breadth parameter and power-law parameter, respectively.

The LCBI is thus rewritten as $$LCBI = \frac{0.5747 * (\eta_0)^{0.19714}}{5.25 * 10^{-4} (M_w)^{0.76}} - 1$$

In order to increase the accuracy in estimating zero shear viscosity, a frequency sweep experiment having a typical range of 0.1-250 rad/s, is combined with a creep experiment, in order to extend the frequency range to values down to $10^{-4}$ $s^{-1}$ or lower, and taking the usual assumption of equivalence of angular frequency (rad/s) and shear rate.

Frequency sweep experiments are performed using small parallel plates having a diameter of 8 mm that allow flow curve determination with as little as 0.1 g PE. Also, most tests are conducted at a temperature of 230° C. for polymers that do not exhibit homogeneous flow below that temperature.

Thus, LCBI is derived at a temperature of 230° C. using extrapolated shear viscosity at 0.001 $s^{-1}$ as follows.

$$LCBI_{230} = \frac{0.58 * (\eta_{0.001})^{0.2096}}{5.25 * 10^{-4} (M_w)^{0.76}} - 1$$

The subscript 230 recalls that LCBI is determined from frequency sweep experiments conducted at 230° C.

The relationship between viscosity and Mw is established as usual with a series of linear polyethylene. The viscosity/Mw relationship was established with a series of 15 linear PE having a polydispersity index between 2 and 18.

ZN or metallocene-produced polyethylene known to be linear have a LCBI of 0+/−0.1. Thus, PE with LCB are detected above LCBI of 0.1-0.2

EXAMPLES

Preparation of Ligands

Preparation of 2-naphtylamine

In a sealed reactor, 4.32 g (30 mmol, 1 eq) of 2-naphthol, 2.85 g (30 mmol, 1 eq) of $(NH_4)_2SO_3$ and 50 mL of aqueous ammonia were mixed. The mixture was heated to 150° C., the pressure was raised to 10 bars and the mixture was stirred overnight. The mixture was then cooled down to room temperature.

The brown solid was filtered, washed with water, and dissolved in a mixture of 30 mL of EtOH, 20 mL of $H_2O$ and 7 mL of HCl 37% at a temperature of 70° C. The solution was treated with 1.5 g of charcoal at 70° C. during one hour and then filtered. The aqueous phase was washed with 20 mL of toluene and neutralised by adding 10 mL of aqueous ammonia, followed by extraction with 3×40 mL of toluene at 70° C. The organic phase was washed with 40 mL of water, dried over $MgSO_4$ and concentrated. 3.29 g pink solid were obtained with a yield of 77%.

$^1$H-RMN (500 MHz, $CDCl_3$) results: δ=3.87 (br s, 2H), 6.98 (dd, 1H), 7.02 (d, 1H), 7.25 (t, 1H), 7.39 (t, 1H), 7.62 (d, 1H), 7.69 (d, 1H), 7.72 (d, 1H).

$^{13}$C-RMN (125 MHz, $CDCl_3$) results: δ=109.0, 118.6, 122.8, 126.2, 126.7, 128.1, 128.3, 129.6, 135.31, 144.5

Bisnaphtyldiamine 0.286 g (2 mmol, 1 eq) of 2-naphthylamine and 0.402 g (3 mmol, 1.5 eq) of copper chloride were dissolved in 10 mL of methanol. The reaction mixture was stirred at room temperature for 2 days.

The resulting solid was filtered off and washed with methanol, and then dissolved in 10 mL of water. The solution was warmed to reflux to yield a white solid. Upon addition of a few drops of ammonia, the solution turned blue and a white precipitate appeared. The reaction mixture was cooled down to room temperature and stirring was stopped. The solid was filtered off, dissolved in dichloromethane and dried over $MgSO_4$ and then concentrated to dryness.

0.183 g of pink solid were obtained with a yield of 64%.

$^1$H-RMN (300 MHz, $CDCl_3$) results: δ=3.51 (br s, 4H), 7.08-7.27 (m, 8H), 7.80-7.85 (m, 4H).

$^{13}$C-RMN (125 MHz, $CDCl_3$) results: δ=111.3, 119.4, 121.9, 124.0, 126.9, 128.1, 128.9, 129.4, 134.4, 144.9.

Synthesis of Dialdimines.

1 mmol of bisnaphthyldiamine and 2 mmol of the desired aldehyde were dissolved in toluene. After addition of a 4 angström molecular sieves, the reaction mixture was stirred at a temperature of 110° C. for a period of time of 2 days. Molecular sieves were filtered off and the solvent was removed in vacuum. The resulting solid was crystallised from MeOH to give a yellow solid. Depending upon the nature of the aldehyde utilised, various compounds were obtained and characterised by NMR.

Bis-naphthyldi(benzaldimine) (L2)

Yield=46%

$^1$H-RMN (500 MHz, $CD_2Cl_2$) results: δ=7.29-7.47 (m, 18H), 7.97 (d, 2H), 8.03 (d, 2H), 8.29 (s, 2H)

$^{13}$C-RMN (125 MHz, $CD_2Cl_2$) results: δ=119.5, 126.7, 126.8, 127.5, 127.6, 128.4, 128.7, 128.8, 129.5, 131.4, 132.0, 133.8, 136.7, 149.3, 161.1.

Bis-naphthyldi(2,6-dimethylbenzaldimine) (L3)

Yield=49%

$^1$H-RMN (500 MHz, $CD_2Cl_2$) results: δ=1.98 (s, 12H), 6.90 (d, 4H), 7.06 (t, 2H), 7.31-7.44 (m, 8H), 7.96 (d, 2H), 8.05 (d, 2H), 8.79 (s, 2H).

$^{13}$C-RMN (125 MHz, $CD_2Cl_2$) results: δ=20.6, 119.7, 125.2, 126.4, 126.8, 126.9, 128.4, 128.9, 129.4, 129.7, 132.2, 133.6, 133.9, 138.8, 149.7, 161.3.

Bis-naphthyldi(2,4,6-trimethylbenzaldimine) (L4)

Yield=91%
$^1$H-RMN (500 MHz, CD$_2$Cl$_2$) results: δ=1.95 (s, 12H), 2.21 (s, 6H), 6.72 (s, 4H), 7.29-7.41 (m, 8H), 7.94 (d, 2H), 8.01 (d, 2H), 8.75 (s, 2H).
$^{13}$C-RMN (125 MHz, CD$_2$Cl$_2$) results: δ=20.7, 21.2, 119.7, 125.0, 126.4, 126.7, 126.9, 128.2, 129.2, 129.8, 130.6, 132.1, 133.9, 138.7, 139.9, 149.9, 161.0.

Bis-naphthyldi(2,4-dimethoxybenzaldimine) (L5)

Yield=50%
$^1$H-RMN (500 MHz, CD$_2$Cl$_2$) results: δ=3.67 (s, 6H), 3.80 (s, 6H), 6.36 (d, 4H), 7.25-7.50 (m, 11H), 7.93 (d, 2H), 7.99 (d, 2H), 8.59 (s, 2H)
$^{13}$C-RMN (125 MHz, CD$_2$Cl$_2$) results: δ=55.7, 97.9, 105.7, 118.6, 120.3, 124.7, 126.4, 126.6, 126.8, 128.3, 128.7, 129.1, 131.7, 133.9, 150.3, 156.6, 161.1, 163.8.

Bis-naphthyldi(4-methoxybenzaldimine) (L6)

Yield=60%
$^1$H-RMN (500 MHz, CD$_2$Cl$_2$) results: δ=3.82 (s, 6H), 6.84 (d, 4H), 7.26-7.43 (m, 12H), 7.95 (d, 2H), 8.01 (d, 2H), 8.18 (s, 2H).
$^{13}$C-RMN (125 MHz, CD$_2$Cl$_2$) results: δ=55.7, 114.2, 119.7, 124.9, 126.4, 126.4, 126.7, 128.3, 129.3, 129.7, 130.3, 131.8, 133.8, 149.6, 160.4, 162.4.

Bis-naphthyldi(4-chlorobenzaldimine) (L7)

Yield=48.2%
$^1$H-RMN (500 MHz, CD$_2$Cl$_2$) results: δ=7.28-7.45 (m, 16H), 7.93 (d, 2H), 7.98 (d, 2H), 8.19 (s, 2H)
$^{13}$C-RMN (125 MHz, CD$_2$Cl$_2$) results: δ=119.2, 125.3, 126.8, 126.9, 127.1, 128.4, 129.2, 129.7, 129.8, 129.9, 132.2, 133.7, 135.2, 137.3, 148.8, 159.6

Bis-naphthyldi(2,4-dichlorobenzaldimine) (L8)

Yield=74%
$^1$H-RMN (300 MHz, CD$_2$Cl$_2$) results: δ=7.07 (d, 2H), 7.24-7.30 (m, 6H), 7.37 (d, 2H), 7.39 (t, 2H), 7.49 (d, 2H) 7.92 (d, 2H), 7.98 (d, 2H), 8.61 (s, 2H).
$^{13}$C-RMN (75 MHz, CD$_2$Cl$_2$) results: δ=120.8, 127.0, 128.4, 128.6, 129.4, 129.9, 130.1, 131.2, 131.3, 133.7, 133.8, 135.3, 138.1, 139.1, 150.0, 157.9.

Bis-naphthyldi(9-anthracenylaldimine) (L9)

Yield=53%

$^1$H-RMN (300 MHz, CD$_2$Cl$_2$) results: δ=7.08 (t, 4H), 7.36 (m, 6H), 7.47 (m, 4H), 7.70 (d, 2H), 7.88 (d, 4H), 8.06 (m, 6H), 8.20 (d, 2H), 8.38 (s, 2H), 9.60 (s, 2H)

$^{13}$C-RMN (75 MHz, CD$_2$Cl$_2$) results: δ=120.2, 125.1, 125.7, 125.8, 126.8, 127.3, 127.5, 128.7, 129.2, 130.1, 130.8, 130.9, 131.6, 132.7, 149.8, 161.1

Bis-naphthyldi(9-phenanthrylaldimine) (L10)

Yield=76%

$^1$H-RMN (300 MHz, CD$_2$Cl$_2$) results: δ=7.0 (t, 2H), 7.36 (t, 2H), 7.45-7.69 (m, 12H), 7.7-7.8 (4H, m), 8.0 (d, 2H), 8.1 (d, 2H), 8.3 (d, 2H), 8.57 (d, 4H), 8.87 (s, 2H)

$^{13}$C-RMN (75 MHz, CD$_2$Cl$_2$) results: δ=118.9, 123.0, 123.1, 125.7, 126.7, 127.2, 127.4, 127.5, 127.9, 128.7, 128.9, 130.0, 131.0, 131.3, 132.7, 134.3, 134.4, 149.1, 149.8, 161.5

Bis-naphthyldi(2,5-trifluoromethylbenzaldimine) (L11)

Yield=93%

$^1$H-RMN (300 MHz, CD$_2$Cl$_2$) results: δ=7.31 (m, 4H), 7.43 (m, 4H), 7.5-7.76 (m, 6H), 7.94 (d, 2H), 8.03 (d, 2H), 8.69 (m, 2H)

$^{13}$C-RMN (125 MHz, CD$_2$Cl$_2$) results: δ=118.3, 122.3, 122.6, 125.7, 125.9, 126.8, 126.9, 127.1, 127.3, 128.1, 128.5, 129.9, 132.8, 133.8, 134.3, 135.6, 146.9, 154.5.

Bis-naphthyldi(2,6-nitrobenzaldimine) (L12)

Yield=70%

$^1$H-RMN (300 MHz, CD$_2$Cl$_2$) results: δ=7.08 (d, 2H), 7.2 (t, 2H), 7.39-7.56 (m, 6H), 7.90-8.05 (m, 8H), 8.87 (s, 2H)

$^{13}$C-RMN (125 MHz, CD$_2$Cl$_2$) results: δ=98.2, 119.9, 127.3, 128.0, 128.2, 129.6, 129.9, 131.2, 131.6, 132.2, 134.4, 134.9, 148.4, 155.4

Synthesis of Diketimines.

1 mmol of bisnaphthyldiamine and 2 mmol of ketone were dissolved in 10 mL of anhydrous toluene. After addition of activated 4 angstrom molecular sieves by 10 g portions, the reaction mixture was stirred at a temperature of 110° C. for a period of time of 2 days. Molecular sieves were filtered off and the solvent was removed in vacuum. The resulting solid was crystallised from MeOH to give the resulting solid. Several compounds were obtained and characterised.

Bis-naphthyldi(9-fluorenylimine) (L13)

Yield=68%

$^1$H-RMN (300 MHz, CD$_2$Cl$_2$) results: δ=6.0 (m, 4H), 6.41 (d, 4H), 6.73 (t, 8H), 7.0-7.50 (m, 24H), 7.85 (d, 4H), 7.94 (d, 4H).

$^{13}$C-RMN (75 MHz, CD$_2$Cl$_2$) results: δ=163.3, 149.0, 143.4, 142.2, 138.2, 133.6, 131.9, 131.6, 131.5, 129.5, 129.1, 128.7, 128.5, 128.1, 127.5, 127.2, 126.9, 126.4, 125.8, 125.2, 124.4, 123.4, 120.9, 119.8, 119.7

Bis-naphthyldi(phenylmethyleneimine) (L1)

Yield=74%

$^1$H-RMN (300 MHz, CD$_2$Cl$_2$) results: δ=6.64 (d, 2H), 6.74-6-78 (m, 8H), 6.93-6.97 (m, 4H), 7.05 (t, 2H), 7.19-7.48 (m, 6H), 7.50 (t, 2H), 7.68 (d, 6H), 7.77 (d, 2H)

$^{13}$C-RMN (75 MHz, CD$_2$Cl$_2$) results: δ=122.2, 124.1, 124.2, 126.1, 126.5, 127.8, 127.9, 128.0, 128.2, 128.3, 128.9, 130.0, 130.2, 130.6, 130.7, 133.9, 136.6, 140.8, 147.6, 167.2

Bis-naphthyldi(4-chlorophenylmethyleneimine) (L14)

Yield=43%

$^1$H-RMN (300 MHz, CD$_2$Cl$_2$) results: δ=6.19 (d, 2H), 6.40 (d, 4H), 6.64 (d, 4H), 6.79 (t, 2H), 7.18 (t, 2H), 7.27 (d, 4H), 7.49 (d, 2H), 7.65-7.75 (m, 8H).

Bis-naphthyl(methyl-(2-naphthyl)methylenimine) (L15)

Yield=75%

$^1$H-RMN (300 MHz, CD$_2$Cl$_2$) results: δ=2.27 (s, 6H), 7.06 (d, 2H), 7.28-7.46 (m, 12H), 7.58-7.65 (m, 4H), 7.75 (m, 4H), 7.87 (m, 4H)

$^{13}$C-RMN (75 MHz, CD$_2$Cl$_2$) results: δ=165.0, 148.1, 137.7, 134.6, 134.0, 133.301, 131.3, 129.2, 128.8, 128.5, 128.0, 128.0, 127.8, 127.5, 126.7, 126.6, 126.5, 124.7, 124.6, 123.7, 121.0

Bis-naphthyldi(adamtylmethylenimine) (L16)

Yield=83%

$^1$H-RMN (300 MHz, CD$_2$Cl$_2$) results: δ=0.99 (2H, m), 1.17-1.97 (22H, m), 2.26-2.68 (4H, m), 6.90-6.99 (2H, m), 7.13 (4H, m), 7.28 (2H, m), 7.77-7.82 (4H, m)

$^{13}$C-RMN (75 MHz, CD$_2$Cl$_2$) results: δ=28.25, 28.48, 36.89, 37.02, 39.78, 40.1, 43.19, 121.68, 124.10, 126.15, 126.46, 128.33, 128.39, 129.33, 130.91, 134.41, 147.56, 180.42.

Synthesis of Ni(II) Complexes.

1 mmol of dialdimine or diketimine ligand was dissolved in 10 mL of dichloromethane, and 1 mmol of dibromide dimethoxyethane nickel (Ni(DME)Br$_2$) complex was added to the mixture. After stirring overnight at room temperature, the mixture was filtered through a celite pad. The solution was concentrated and pentane was added to give a precipitate. Solvents were filtered off and the solid was washed twice with pentane. The resulting solid was dried under vacuum, to afford a powder of the nickel complex.

Ligand L1 gave Ni complex 1 with a yield of 78%.

Ligand L2 gave Ni complex 2 with a yield of 78%.

Ligand L3 gave Ni complex 3 with a yield of 69%.

Ligand L4 gave Ni complex 4 with a yield of 72%.

Ligand L5 gave Ni complex 5 with a yield of 39%.

Ligand L6 gave Ni complex 6 with a yield of 62%.

Ligand L7 gave Ni complex 7 with a yield of 42%.

Ligand L8 gave Ni complex 8 with a yield of 77%.

Ligand L9 gave nickel complex 9 with a yield of 57%.

Ligand L10 gave nickel complex 10 with a yield of 51%.

Ligand L11 gave nickel complex 11 with a yield of 55%.

Ligand L12 gave nickel complex 12 with a yield of 9%.

Ligand L13 gave nickel complex 13 with a yield of 43%.

Ligand L16 gave nickel complex 16 with a yield of 80%.

Ligand L14 gave nickel complex 14 with a yield of 60%.

Synthesis of Co(II) Complexes.

1 mmol of dialdimine or diketimine ligand was dissolved in 10 mL of dry dichloromethane and 1 mmol of cobalt (II) chloride was added. The mixture was stirred under argon overnight at room temperature. The solid was filtered off and the filtrate was concentrated under vacuum to approximately 2 mL. 20 mL of dry pentane were added to precipitate the complex. The solvent was removed by filtration under argon and the resulting powder was washed twice with 5 mL of dry pentane. The solid was dried under vacuum to afford Co(II) complex as a powder.

Ligand L17 gave cobalt complex 17 with a yield of 69%.

Ligand L15 gave nickel complex 15 with a yield of 82%.

Ligand L18 gave cobalt complex 18 with a yield of 99%.

Synthesis of Cr(III) Complexes.

1 mmol of dialdimine or diketimine ligand was dissolved in 10 mL of dry tetrahydrofuran and 1 mmol of chromium (III) chloride tetrahydrofuran complex was added to the mixture.

After stirring overnight at room temperature, the mixture was filtered and the filtrate concentrated to dryness. The solid was washed twice with pentane. The resulting solid was dried under vacuum to afford Cr(III) complex as a powder.

Ligand L19 gave chromium complex 19 with a yield of 74%.

Ligand L20 gave chromium complex 20 with a yield of 91%.

Ligand L21 gave chromium complex 21 with a yield of 77%.

Ligand L5 gave chromium complex 21 b with a yield of 93%.

Synthesis of Fe(II) and Fe(III) Complexes.

1 mmol of iron (II) chloride complex (FeCl$_2$.4H$_2$O) was dried at 120° C., under vacuum, for 1 h. 1 mmol of dialdimine or diketimine ligand was dissolved in 10 mL of dry tetrahydrofuran and added to the complex at room temperature. After stirring overnight at room temperature, the mixture was filtered through degased celite and the filtrate concentrated to dryness. The solid was washed twice with 10 ml of pentane. The resulting solid was dried under vacuum to afford Fe(II) complex as a powder.

Ligand L22 gave iron complex 22 with a yield of 71%.

Ligand L23 gave iron complex 23 with a yield of 87%.

Ligand L24 gave iron complex 24 with a yield of 76%.

Ligand L25 gave iron complex 25 with a yield of 86%.

Ligand L26 gave iron complex 26 with a yield of 61%.

Polymerisation or Oligomerisation of Ethylene.

Ethylene oligomerisation reactions were performed in a 20 mL stainless steel autoclave containing a glass insert, fitted with mechanical stirring, external thermocouple and pressure gauge and controlled by computer. In a typical reaction run, 4 mL of dry solvent (toluene or n-heptane) were introduced into the reactor. In a argon-filled glove box, about 4 mg (5 μmol) of the appropriate catalyst were weighted, activated with methylaluminoxane (MAO 30% wt in toluene) or tetraisobutyldialuminoxane (IBAO 10 wt % in toluene) activator in an amount appropriate to obtain a ratio [Al]:[M] of 2000 for MAO and a ratio [Al]:[M] of 500 for IBAO, and diluted with toluene to obtain a final volume of 2 mL. 200 μL of the solution of activated catalyst were placed inside the reactor. The injection loop was rinsed with 800 μL of solvent. The temperature was set to 50° C. The ethylene pressure was raised to 15 bar and continuously fed. After 1 h or an ethylene consumption of 12 mmol, the reaction was quenched with isopropanol and the solution analysed by gas chromatography. The gas chromatographic (GC) analysis of the reaction products was performed on a Trace GC apparatus with a Petrocol capillary column (methyl silicone, 100 m long, i.d. 0.25 mm and film thickness of 0.5 μm) working at a temperature of 35° C. for 15 min and then heating at a rate of 50 per minute up to a temperature of 250° C. The remaining reaction mixture was quenched with MeOH/HCl and the polymer was filtered, washed with methanol and dried for a period of time of 24 hours under vacuum at a temperature of 50° C. The reaction conditions are displayed in Table I and the polymerisation and oligomerisation results are displayed in Table II, III and IV.

TABLE I

| Run | Complex | Amt cata nmol | Time min | Solvent | Activator |
|---|---|---|---|---|---|
| 1 | 1 | 510 | 54 | toluene | MAO |
| 2 | 2 | 498 | 43 | toluene | MAO |
| 3 | 3 | 531 | 41 | toluene | MAO |
| 4 | 4 | 526 | 38 | toluene | MAO |
| 7 | 5 | 526 | 37 | toluene | MAO |
| 6 | 6 | 501 | 43 | toluene | MAO |
| 5 | 8 | 490 | 60 | toluene | MAO |
| 8 | 9 | 512 | 39 | toluene | MAO |
| 9 | 10 | 512 | 46 | toluene | MAO |
| 10 | 11 | 505 | 60 | toluene | MAO |
| 11 | 13 | 532 | 60 | toluene | MAO |
| 12 | 1 | 529 | 60 | n-heptane | MAO |
| 13 | 2 | 515 | 60 | n-heptane | MAO |
| 14 | 3 | 463 | 60 | n-heptane | MAO |
| 15 | 4 | 511 | 60 | n-heptane | MAO |
| 16 | 5 | 469 | 61 | n-heptane | MAO |
| 17 | 6 | 541 | 60 | n-heptane | MAO |
| 18 | 8 | 490 | 60 | n-heptane | MAO |
| 19 | 9 | 500 | 60 | n-heptane | MAO |
| 20 | 10 | 505 | 60 | n-heptane | MAO |
| 21 | 11 | 505 | 60 | n-heptane | MAO |
| 22 | 13 | 496 | 60 | n-heptane | MAO |
| 23 | 17 | 542 | 60 | toluene | MAO |
| 24 | 18 | 485 | 60 | toluene | MAO |
| 25 | 17 | 508 | 60 | n-heptane | MAO |
| 26 | 18 | 485 | 60 | n-heptane | MAO |
| 27 | 19 | 501 | 29 | toluene | MAO |
| 28 | 20 | 493 | 34 | toluene | MAO |
| 29 | 19 | 501 | 60 | n-heptane | MAO |
| 30 | 20 | 493 | 60 | n-heptane | MAO |
| 31 | 19 | 517 | 60 | n-heptane | IBAO |
| 32 | 20 | 506 | 38 | n-heptane | IBAO |
| 33 | 21 | 495 | 60 | n-heptane | MAO |
| 34 | 21 | 495 | 60 | n-heptane | IBAO |
| 35 | 21b | 514 | 60 | n-heptane | MAO |
| 36 | 21b | 528 | 60 | n-heptane | IBAO |

TABLE II

| | Oligomerisation results with Ni(II) Complexes | | | | | |
|---|---|---|---|---|---|---|
| | Activity | % C4 | | % C6 | | |
| Run | Kg/molNi/h | Total | % α-C4 | Total | % α-C6 | % > C6 |
| 1 | 736 | 85 | 73 | 13 | 21 | 2 |
| 2 | 950 | 82 | 59 | 15 | 18 | 3 |
| 3 | 936 | 80 | 56 | 17 | 17 | 3 |
| 4 | 1012 | 78 | 53 | 18 | 16 | 4 |
| 5 | 1038 | 78 | 54 | 19 | 16 | 3 |
| 6 | 947 | 80 | 56 | 18 | 18 | 3 |
| 7 | 656 | 82 | 60 | 166 | 18 | 2 |

TABLE II-continued

Oligomerisation results with Ni(II) Complexes

| Run | Activity Kg/molNi/h | % C4 Total | % α-C4 | % C6 Total | % α-C6 | % > C6 |
|---|---|---|---|---|---|---|
| 8 | 1022 | 78 | 51 | 19 | 17 | 3 |
| 9 | 848 | 79 | 54 | 18 | 18 | 3 |
| 10 | 523 | 84 | 64 | 14 | 21 | 2 |
| 11 | 318 | 89 | 77 | 10 | 25 | 1 |
| 12 | 138 | 86 | 81 | 10 | 25 | 4 |
| 13 | 167 | 86 | 81 | 10 | 26 | 4 |
| 14 | 150 | 88 | 82 | 10 | 27 | 2 |
| 15 | 194 | 85 | 78 | 11 | 23 | 4 |
| 16 | 158 | 85 | 80 | 11 | 25 | 4 |
| 17 | 136 | 85 | 84 | 10 | 33 | 5 |
| 18 | 93 | 88 | 83 | 10 | 28 | 2 |
| 19 | 139 | 87 | 81 | 10 | 25 | 3 |
| 20 | 167 | 87 | 79 | 10 | 25 | 3 |
| 21 | 92 | 90 | 85 | 9 | 28 | 1 |
| 22 | 76 | traces | — | — | — | — |

In all reactions, 0.5 μmol of catalyst were dissolved in 5 mL of solvent.

The percentages of C4, C6 and >C6 were calculated by GC analysis as well as the percentages of α-C2n in C2n.

TABLE III

Oligomerisation results with Co(II) Complexes

| Run | Activity Kg/molCo/h |
|---|---|
| 23 | 28 |
| 24 | 33 |
| 25 | 27 |
| 26 | 25 |

TABLE IV

Polymerisation results with Cr(III) Complexes

| Run | Activity Kg/molCr/h | PE mg | % C4 Total | % α-C4 | % C6 Total | % α-C6 | % > C6 |
|---|---|---|---|---|---|---|---|
| 27 | 1364* | 13 | 17 | >99.5 | 26 | 96 | 58 |
| 28 | 1189* | 9 | 19 | >99.5 | 27 | 96 | 55 |
| 29 | 120* | 64 | 9 | >99.5 | 18 | 79 | 73 |
| 30 | 129* | 51 | 10 | >99.5 | 18 | 84 | 72 |
| 31 | 1185 | 610 | / | | / | | / |
| 32 | 2520 | 812 | / | | / | | / |
| 33 | 249* | 152 | 9 | >99.9 | 20 | 86 | 71 |
| 34 | 1291 | 639 | / | | / | | / |
| 35 | 101* | 57 | 14 | >99.9 | 23 | 78 | 63 |
| 36 | 529 | 278 | / | | / | | / |

Activity is expressed as kg polyethylene per mol Cr per hour
*Activity is expressed as kg ethylene consumed per mol Cr per hour The percentages of C4, C6 and >C6 were calculated by GC analysis as well as the percentages of α-C2n in C2n.

With IBAO, in runs 31, 32, 34 and 36, a bimodal polyethylene was obtained. Characterisation of the polymers are given in table IVa.

HT-GPC analysis were realised in 1,2,4-trichlorobenzene at 145° C. using polystyrene for calibration.

$^{13}$C NMR analysis were realised in a mixture of trichlorobenzene and d6-benzene at 135° C.

Melting temperature is measured by Differential Scanning Calorimetry (DSC). Samples are placed at room temperature and are than first heated in order to cancel its thermal past. The crystallization and fusion cycles of the sample can then be started. The area of a crystallization or fusion peak provides a measure of transition enthalpy. There is a correlation between enthalpy and density for polyethylene of medium and high density. The conditions used in the present measurements are as follows:

sample weight=5+/−1 mg 1 minute isotherm at 40° C.

heating rate of 20° C./min from 40 to 180° C.

3 minutes isotherm at 200° C.

cooling rate of 20° C./min from 200 to 60° C.

2 minutes isotherm at 60° C.

heating rate of 20° C./min from 60 to 180° C.

TABLE IVa

Characterisation of the polyethylenes obtained with Cr(III) complexes and IBAO.

| | | HT-GPC | | | $^{13}$C NMR | | | DSC |
|---|---|---|---|---|---|---|---|---|
| Run | RDA LCBI | Mw (Da) | Mn (Da) | D | SCB (mol %) | Me ends/ 10000 C. | iBu ends/ 10000 C. | Tm (° C.) |
| 31 | 0.34 | 455401 | 17355 | 26.2 | 0.11 | 9 | 4 | 134.3 |
| 32 | 0.7 | 574924 | 13471 | 42.7 | 0.03 | 17 | 8 | 132.6 |
| 34 | 0.09 | 620000 | 17000 | 36.3 | / | / | / | 133.6 |
| 36 | — | 699806 | 25848 | 27.1 | / | / | / | 134.7 |

Figure 1:
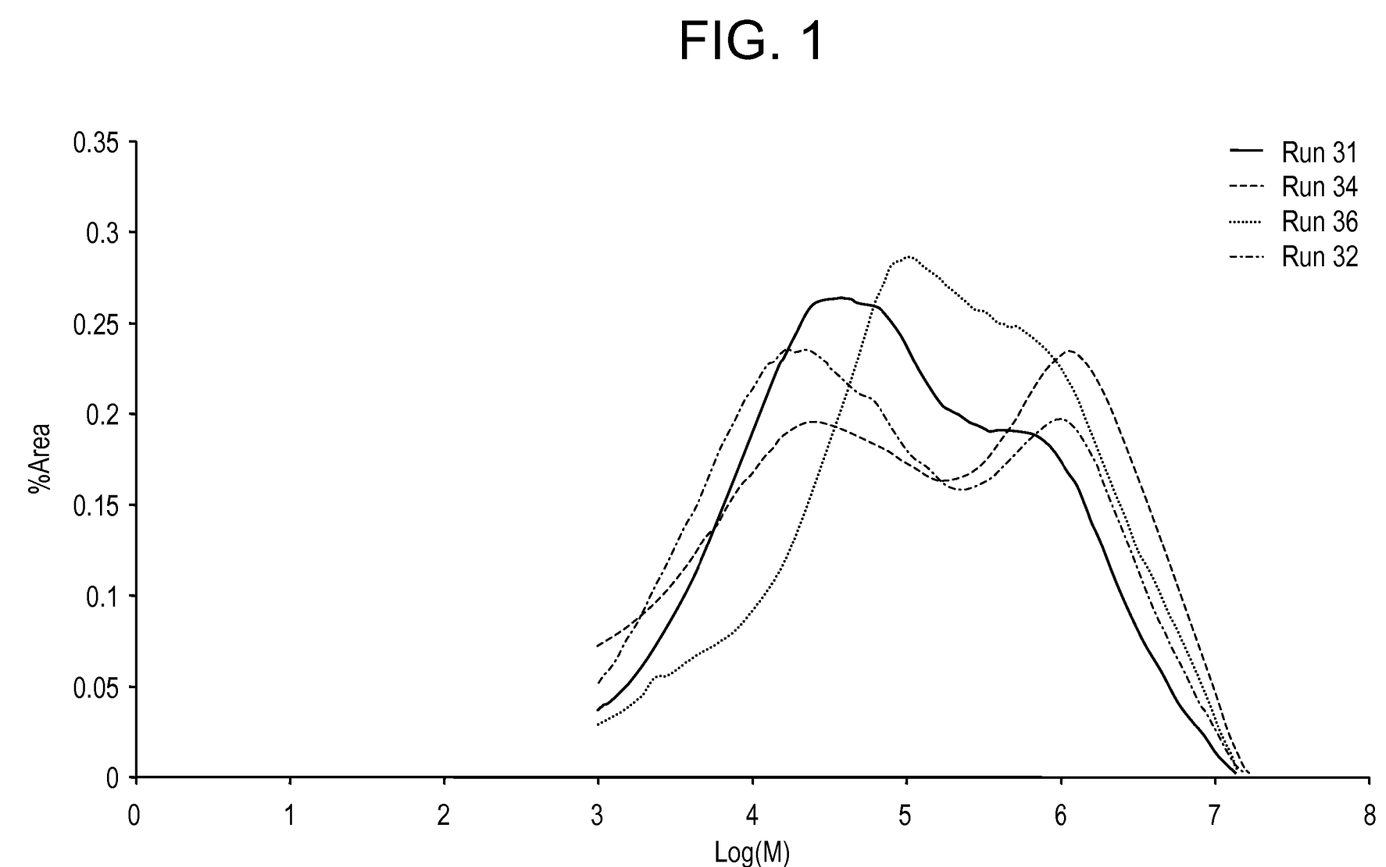

The molecular weight distributions for runs 31, 32, 34 and 36 are represented in FIG. 1.

The resins of the present invention have LCBI values of less than 0.8 typical of medium level of LCB. Their level of LCB is similar to that of Cr resins.

Oligomerisation of 1-Hexene.

In a argon-filled glove box, 6 mg (~7.5 μmol) of the appropriate catalyst were weighted, activated with methylaluminoxane (MAO) activator (30% wt in toluene) in an amount appropriate to obtain a ratio [Al]:[Ni] of 2000 and diluted with toluene to obtain a final volume of 4.5 mL. 3 mL of the solution of the activated catalyst were placed in a Schlenk tube containing 5 mL of 1-hexene (5 mL). The solution was stirred at a temperature of 30° C. for a period of time of 1 h. The mixture was quenched with methanol and slightly acidified water. The layers were separated. The toluene layer was concentrated to dryness to provide oligomers. The gas chromatographic analysis of the reaction products was done on a Trace GC apparatus with a Petrocol capillary column (methyl silicone, 100 m long, i.d. 0.25 mm and film thickness of 0.5 μm) working at a temperature of 100° C. for 4 min and then heating at a rate of 8° C. per minute to a temperature of 250° C. The oligomerisation conditions and results are displayed in Table V.

TABLE V

| Ni complex | Amt cata μmol | Time min | Yield mg | Activity Kg/molNi/h | % C12 | % C18 | % C24 |
|---|---|---|---|---|---|---|---|
| 1 | 5.0 | 60 | 46 | 9 | 63 | 36 | 1 |
| 2 | 5.1 | 60 | 142 | 28 | 77 | 23 | 0 |
| 4 | 5.0 | 60 | 177 | 35 | 85 | 15 | 0 |
| 5 | 5.1 | 60 | 45 | 9 | 67 | 33 | 0 |

Oligomerisation of Ethylene with Supported Catalysts

Ethylene oligomerisation reactions were performed in a 20 mL stainless steel autoclave containing a glass insert, fitted with mechanical stirring, external thermocouple and pressure gauge and controlled by computer. In a typical reaction run, 4.2 mL of dry n-heptane and Tibal (1M in toluene) in an appropriate amount to obtain a ratio [Al]:[M] of 300, were introduced into the reactor. In a argon-filled glove box, about 192 mg (5 μmol) of the appropriate supported catalyst (complex deposited on MAO impregnated silica, at 2 wt % based on the total weight of the supported catalyst) were weighted, and diluted with Vestan oil to obtain a final volume of 2 mL. 200 μL of the solution of activated catalyst were placed inside the reactor. The injection loop was rinsed with 800 μL of n-heptane. The temperature was set to 80° C. The ethylene pressure was raised to 19 bars and continuously fed. After 1 h or an ethylene consumption of 12 mmol, the reaction was quenched with isopropanol and the solution analysed by gas chromatography. The gas chromatographic (GC) analysis of the reaction products was performed on a Trace GC apparatus with a Petrocol capillary column (methyl silicone, 100 m long, i.d. 0.25 mm and film thickness of 0.5 μm) working at a temperature of 35° C. for 15 min and then heating at a rate of 5° per minute up to a temperature of 250° C. The oligomerisation results are displayed in Table VI.

TABLE VI

Oligomerisation results with supported Ni(II) Complexes

| Ni complex | Activity Kg/molNi/h | % C4 | % C6 | % C8 |
|---|---|---|---|---|
| 3 | 53 | 46 | 37 | 17 |
| 4 | 50 | 49 | 37 | 13 |

*Activity is expressed as kg ethylene consumed per mol catalyst per hour

Polymerisation of Ethylene with Supported Catalysts

Ethylene polymerisation reactions were carried out in a 130 ml stainless steel autoclave equipped with mechanical stirring and a stainless steel injection cylinder. In a typical reaction run, the reactor was first dried under nitrogen flow at 100° C. during 10 min. Then it was cooled down to the reaction temperature (50° or 85° C.) and 35 ml of isobutane were introduced into the reactor with a syringe pump, followed by the comonomer if required. The pressure was adjusted to the desired value (14.8 or 23.8 bar) with ethylene. In an argon-filled glove box, 303 mg of the supported catalyst (complex 20 deposited on MAO impregnated silica, at 2 wt % based on the total weight of the supported catalyst), the cocatalyst and 0.6 ml of n-hexane were placed into the injection cylinder. The valve was closed and the cylinder was connected to the reactor under nitrogen flow. The active catalyst mixture was then introduced into the reactor with 40 ml of isobutane. After 30 minutes or 1 hour, the reactor was cooled down to room temperature and slowly depressurized, and the polymer was recovered. The polymerisation results are displayed in Table VII.

TABLE VII

Polymerisation results with supported Cr(III) Complexes

| Cr complex | T (° C.)/ P (bar) | Cocatalyst Cocatalyst | Time min. | PE g | Activity* g/g/h | DSC DSC Tm (° C.) |
|---|---|---|---|---|---|---|
| 20 | 50/ 14.8 | TiBAl 25.6 mg | 30 | 0.9 | 5.6 | 132.3 |
| 20 | 85/ 23.8 | TiBAl 25.6 mg | 30 | 0.8 | 5.3 | / |
| 20 | 85/ 23.8 | TEAl 16.6 mg | 60 | 1.4 | 4.6 | 129.7 |

*Activity is expressed as g ethylene consumed per g catalyst per hour

The obtained polymers could not be characterised by GPC because they were not fully soluble in TCB at 140° C. The $^{13}C$ NMR analysis showed saturated and vinylic ends but no short chain branching (less than 0.1 mol %).

The invention claimed is:

1. A catalyst component represented by the formula wherein $R_1, R_2, R_3, R_4, R_5, R_6, R_7, R_8, R_9, R_{10}, R_{11}$ and $R_{12}$ are each independently selected from hydrogen, unsubstituted or substituted hydrocarbyl, or inert functional group and two or more of groups can be linked together to form further ring or rings; $R_7$ and $R_8$ together, and $R_9$ and $R_{10}$ together, are joined to form naphthyl groups; wherein M is Ti, Zr, Hf, V, Cr, Mn, Fe, Co, or Ni; X is a halogen and n is the valence of M.

2. A catalyst component represented by the formula wherein $R_1, R_2, R_3$ and $R_4$ are unsubstituted or substituted alkyl groups, unsubstituted or substituted aryl-groups or unsubstituted or substituted cycloalkyl groups; wherein $R_5, R_6, R_7, R_8, R_9, R_{10}, R_{11}$ and $R_{12}$ are each independently selected from hydrogen, unsubstituted or substituted hydrocarbyl, or inert functional group and two or more of groups can be linked together to form further ring or rings $R_7$ and $R_8$ together, and $R_9$ and $R_{10}$ together are joined to form naphthyl groups; wherein M is Ti, Zr, Hf, V, Cr, Mn, Fe, Co, or Ni; wherein X is a halogen and n is the valence of M.

3. A catalyst component represented by the formula wherein $R_1, R_2, R_3$ and $R_4$ are unsubstituted or substituted phenyl groups; wherein $R_5, R_6, R_7, R_8, R_9, R_{10}, R_{11}$ and $R_{12}$ are each independently selected from hydrogen, unsubstituted or substituted hydrocarbyl, or inert functional group and two or more of groups can be linked together to form further ring or rings; wherein M is Ti, Zr, Hf, V, Cr, Mn, Fe, Co, or Ni; wherein X is a halogen and n is the valence of M.

4. A catalyst component represented by the formula wherein $R_1, R_2, R_3$ and $R_4$ are phenyl groups substituted by two methyl groups respectively in positions 2 and 6, or by three methyl groups respectively in positions 2, 4 and 6, or by one methoxy group in position 4 or by two methoxy groups respectively in positions 4 and 6; wherein $R_5, R_6, R_7, R_8, R_9, R_{10}, R_{11}$ and $R_{12}$ are each independently selected from hydrogen, unsubstituted or substituted hydrocarbyl, or inert functional group and two or more of groups can be linked together to form further ring or rings; wherein M is Ti, Zr, Hf, V, Cr, Mn, Fe, Co, or Ni; wherein X is a halogen and n is the valence of M.

5. A method for preparing the catalyst component of formula IV (IV)

by condensation reaction of the ligand of formula I (I)

and a metallic salt $MX_n$ in a solvent wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, unsubstituted or substituted hydrocarbyl, or inert functional group and two or more of groups can be linked together to form further ring or rings $R_7$ and $R_8$ together, and $R_9$ and $R_{10}$ together are joined to form naphthyl groups; wherein M is Cr or Ni; X is halogen or substituted or unsubstituted hydrocarbyl and n is the valence of M.

* * * * *